(12) United States Patent
Yin

(10) Patent No.: US 8,557,862 B2
(45) Date of Patent: Oct. 15, 2013

(54) SYNERGISTIC ANTIMICROBIAL COMPOSITION

(75) Inventor: Bei Yin, Buffalo Grove, IL (US)

(73) Assignee: Dow Global Technologies LLC, Midland, MI (US)

( * ) Notice: Subject to any disclaimer, the term of this patent is extended or adjusted under 35 U.S.C. 154(b) by 83 days.

(21) Appl. No.: 13/496,953

(22) PCT Filed: Sep. 15, 2010

(86) PCT No.: PCT/US2010/048850
§ 371 (c)(1),
(2), (4) Date: Mar. 19, 2012

(87) PCT Pub. No.: WO2011/041098
PCT Pub. Date: Apr. 7, 2011

(65) Prior Publication Data
US 2012/0178800 A1    Jul. 12, 2012

Related U.S. Application Data

(60) Provisional application No. 61/277,899, filed on Sep. 30, 2009.

(51) Int. Cl.
*A01N 43/32* (2006.01)
*A01P 1/00* (2006.01)

(52) U.S. Cl.
USPC .......................................................... 514/452

(58) Field of Classification Search
USPC .......................................................... 514/452
See application file for complete search history.

(56) References Cited

U.S. PATENT DOCUMENTS 3,469,002 A    9/1969    Moyer, Jr. et al.

*Primary Examiner* — Raymond Henley, III
(74) *Attorney, Agent, or Firm* — Kenneth Crimaldi

(57) ABSTRACT

A synergistic antimicrobial composition having two components. The first component is glutaraldehyde. The second component is 2,6-dimethyl-1,3-dioxan-4-yl acetate.

6 Claims, No Drawings

SYNERGISTIC ANTIMICROBIAL COMPOSITION

This invention relates to combinations of biocides, the combinations having greater activity than would be observed for the individual antimicrobial compounds.

Use of combinations of at least two antimicrobial compounds can broaden potential markets, reduce use concentrations and costs, and reduce waste. In some cases, commercial antimicrobial compounds cannot provide effective control of microorganisms, even at high use concentrations, due to weak activity against certain types of microorganisms, or relatively slow antimicrobial action, or instability under certain conditions such as high temperature and high pH. Combinations of different antimicrobial compounds are sometimes used to provide overall control of microorganisms or to provide the same level of microbial control at lower use rates in a particular end use environment. For example, U.S. Pat. No. 3,469,002 discloses the combination of 6-acetoxy-2,4-dimethyl-m-dioxane and paraformaldehyde, but this reference does not suggest any of the combinations claimed herein. Moreover, there is a need for additional combinations of antimicrobial compounds having enhanced activity to provide effective control of the microorganisms. The problem addressed by this invention is to provide such additional combinations of antimicrobial compounds.

STATEMENT OF THE INVENTION

The present invention is directed to a synergistic antimicrobial composition comprising: (a) glutaraldehyde; and (b) 2,6-dimethyl-1,3-dioxan-4-yl acetate (DXN); wherein a weight ratio of glutaraldehyde to 2,6-dimethyl-1,3-dioxan-4-yl acetate is from 9:1 to 1:15.

DETAILED DESCRIPTION OF THE INVENTION

As used herein, the following terms have the designated definitions, unless the context clearly indicates otherwise. The term "antimicrobial compound" refers to a compound capable of inhibiting the growth or propagation of microorganisms, and/or killing microorganisms; antimicrobial compounds include bactericides, bacteristats, fungicides, fungistats, algaecides and algistats, depending on the dose level applied, system conditions and the level of microbial control desired. The term "microorganism" includes, for example, fungi (such as yeast and mold), bacteria and algae. The following abbreviations are used throughout the specification: ppm=parts per million by weight (weight/weight), mL=milliliter, Unless otherwise specified, temperatures are in degrees centigrade (° C.), and references to percentages are by weight (wt %). Percentages of antimicrobial compounds in the composition of this invention are based on the total weight of active ingredients in the composition, i.e., the antimicrobial compounds themselves, exclusive of any amounts of solvents, carriers, dispersants, stabilizers or other materials which may be present. 2,6-dimethyl-1,3-dioxan-4-yl acetate (DXN) is the same compound as reported in earlier references using the name 6-acetoxy-2,4-dimethyl-m-dioxane.

In some embodiments of the invention, a weight ratio of glutaraldehyde to 2,6-dimethyl-1,3-dioxan-4-yl acetate is from 9:1 to 1:12, alternatively from 9:1 to 1:10, alternatively from 9:1 to 1:9, alternatively from 3:1 to 1:12, alternatively from 3:1 to 1:10, alternatively from 3:1 to 1:9, alternatively from 1:1 to 1:10, alternatively from 1:1 to 1:9; alternatively from 1:2 to 1:10, alternatively from 1:2 to 1:9. In some embodiments of the invention, the composition is used to prevent microbial growth in a medium at higher temperatures and high sulfide levels, i.e., at least 50° C. and 2 ppm sulfide, conditions which typically are present in oil and gas wells. In some embodiments of the invention, a higher temperature and high-sulfide medium is one having a temperature at least 60° C. and a sulfide level at least 4 ppm. In some embodiments, the temperature is at least 65° C.; alternatively at least 70° C.; alternatively at least 75° C.; alternatively at least 80° C. In some embodiments, the medium contains at least 5 ppm sulfide, alternatively at least 6 ppm sulfide, alternatively at least 7 ppm sulfide, alternatively at least 8 ppm sulfide, alternatively at least 9 ppm sulfide, alternatively at least 10 ppm sulfide. In some embodiments of the invention, the high-temperature and high-sulfide environment is anaerobic. In some embodiments of the invention, the medium to which the antimicrobial composition is added contains sulfate-reducing bacteria. In some embodiments of the invention, the high-temperature and high-sulfide environment contains sulfate-reducing bacteria. In some embodiments of the invention, the medium to which the antimicrobial composition is added is an aqueous medium, i.e., one comprising at least 60% water, alternatively at least 80% water. In some embodiments of the invention, the aqueous medium is a high-temperature and high-sulfide medium.

In some embodiments of the invention, the antimicrobial combination of this invention is useful in oil and gas field injection, produced fluids, fracturing fluids and other functional fluids, oil and gas wells, oil and gas operation, separation, storage, and transportation systems, oil and gas pipelines, oil and gas vessels, and fuel. The combination is especially useful in aqueous fluids added to or produced by oil and gas well. The composition also is useful for controlling microorganisms in other industrial water and water containing/contaminated matrixes, such as cooling water, air washer, heat exchangers, boiler water, pulp and paper mill water, other industrial process water, ballast water, wastewater, metalworking fluids, latex, paint, coatings, adhesives, inks, tape joint compounds, pigment, water-based slurries, personal care and household products such as detergent, filtration systems (including reverse osmosis and ultrafiltration systems), toilet bowel, textiles, leather and leather production system, or a system used therewith.

Typically, the amount of the biocide combinations of the present invention to control the growth of microorganisms is from 10 ppm to 5,000 ppm active ingredient. In some embodiments of the invention, the active ingredients of the composition are present in an amount of at least 20 ppm, alternatively at least 50 ppm, alternatively at least 100 ppm, alternatively at least 150 ppm, alternatively at least 200 ppm. In some embodiments, the active ingredients of the composition are present in an amount of no more than 2,000 ppm, alternatively no more than 1,000 ppm, alternatively no more than 500 ppm, alternatively no more than 400 ppm, alternatively no more than 300 ppm, alternatively no more than 250 ppm, alternatively no more than 200 ppm, alternatively no more than 100 ppm, alternatively no more than 50 ppm. Concentrations mentioned above are in a liquid composition containing the biocide combinations. Biocide concentrations in a high-sulfide and high-temperature environment typically will be higher than in other environments. In some embodiments of the invention, active ingredient concentrations downhole in an oil well are from 30 to 500 ppm, alternatively from 50 to 250 ppm. In some embodiments of the invention, active ingredient concentrations for top side treatment at an oil well are from 10 to 300 ppm, alternatively from 30 to 100 ppm.

The present invention also encompasses a method for preventing microbial growth in the use areas described above, especially in oil or natural gas production operations, by incorporating the claimed biocide combination into the materials.

EXAMPLES

Example 1

Synergistic Effect of Glutaraldehyde (Glut) and DXN against Sulfate Reducing Bacteria (SRB)

Inside an anaerobic chamber (BACTRON III), a deaerated sterile salt solution (3.1183 g of NaCl, 1.3082 mg of $NaHCO_3$, 47.70 mg of KCl, 72.00 mg of $CaCl_2$, 54.49 mg of $MgSO_4$, 172.28 mg of $Na_2SO_4$, 43.92 mg of $Na_2CO_3$ in 1 L water) was contaminated with an oil field isolated anaerobic SRB consortium at final bacterial concentrations of $10^6$ to $10^7$ CFU/mL. The aliquots of this contaminated water were then treated with glutaraldehyde and DXN, or the glutaraldehyde/DXN combination at different active concentration levels. After the mixtures were incubated at 40° C. for 24 hour, the biocidal efficacy was determined by minimum tested biocide concentration for complete bacteria kill in the aliquots (MBC). Table 1 summarizes the efficacy of each biocide and their blends, and the Synergy Index* of each combination.

TABLE 1

Biocidal efficacy of glutaraldehyde, DXN, glutaraldehyde/DXN combination, and Synergy Index

| Ratio of glut to DXN (active w/w) | MBC (active ppm) | | Synergy Index*[1] | p value in z test*[2] |
|---|---|---|---|---|
| | glut | DXN | | |
| 1:0 | 2.63 | 0.0 | | |
| 9:1 | 2.62 | 0.29 | 0.99 | 0.00 |
| 3:1 | 2.58 | 0.86 | 0.98 | 0.00 |
| 1:1 | 2.48 | 2.48 | 0.95 | 0.00 |
| 1:3 | 2.23 | 6.70 | 0.87 | 0.00 |
| 1:9 | 1.71 | 15.39 | 0.70 | 0.00 |
| 0:1 | 0.0 | 333.33 | | |

*[1]Synergy Index = Ca/CA + Cb/CB
Ca: Concentration of biocide A required to achieve a complete bacterial kill when used in combination with biocide B
CA: Concentration of biocide A required to achieve a complete bacterial kill when used alone
Cb: Concentration of biocide B required to achieve a complete bacterial kill when used in combination with biocide A
CB: Concentration of biocide B required to achieve a complete bacterial kill when used alone
SI values below 1 indicate synergy
*[2]P value < 0.05 means there is a significant difference between the SI value and 1.00

The invention claimed is:

1. A synergistic antimicrobial composition comprising: (a) glutaraldehyde; and (b) 2,6-dimethyl-1,3-dioxan-4-yl acetate; wherein a weight ratio of glutaraldehyde to 2,6-dimethyl-1,3-dioxan-4-yl acetate is from 9:1 to 1:15.

2. The composition of claim 1 in which the weight ratio is from 9:1 to 1:10.

3. A method for inhibiting microbial growth in a medium at a temperature of at least 60° C. and a sulfide level at least 4 ppm; said method comprising adding to the medium: (a) glutaraldehyde; and (b) 2,6-dimethyl-1,3-dioxan-4-yl acetate; wherein a weight ratio of glutaraldehyde to 2,6-dimethyl-1,3-dioxan-4-yl acetate is from 9:1 to 1:15.

4. The method of claim 3 in which the temperature is at least 70° C. and a sulfide level at least 7 ppm.

5. The method of claim 4 in which the weight ratio is from 9:1 to 1:10.

6. The method of claim 5 in which the medium is anaerobic and contains sulfate-reducing bacteria.

* * * * *